(12) United States Patent
Leung et al.

(10) Patent No.: US 11,344,496 B2
(45) Date of Patent: May 31, 2022

(54) METHODS FOR PREPARING STABILIZED AMORPHOUS DRUG FORMULATIONS USING ACOUSTIC FUSION

(71) Applicant: Merck Sharp & Dohme Corp., Rahway, NJ (US)

(72) Inventors: Dennis H. Leung, Half Moon Bay, CA (US); Zhiqiang Guo, Morganville, NJ (US); Christopher W. Boyce, Flemington, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/641,480

(22) PCT Filed: Aug. 20, 2018

(86) PCT No.: PCT/US2018/047015
§ 371 (c)(1),
(2) Date: Feb. 24, 2020

(87) PCT Pub. No.: WO2019/040346
PCT Pub. Date: Feb. 28, 2019

(65) Prior Publication Data
US 2021/0154138 A1 May 27, 2021

Related U.S. Application Data

(60) Provisional application No. 62/550,025, filed on Aug. 25, 2017.

(51) Int. Cl.
| | | |
|---|---|---|
| *A61K 9/10* | (2006.01) | |
| *A61K 9/14* | (2006.01) | |
| *A61K 31/421* | (2006.01) | |
| *A61K 31/47* | (2006.01) | |
| *A61K 31/496* | (2006.01) | |
| *A61K 31/513* | (2006.01) | |
| *A61K 47/32* | (2006.01) | |
| *A61K 47/38* | (2006.01) | |

(52) U.S. Cl.
CPC ............... *A61K 9/10* (2013.01); *A61K 9/146* (2013.01); *A61K 31/421* (2013.01); *A61K 31/47* (2013.01); *A61K 31/496* (2013.01); *A61K 31/513* (2013.01); *A61K 47/32* (2013.01); *A61K 47/38* (2013.01)

(58) Field of Classification Search
CPC .......................................................... A61K 9/10
USPC ..................................................... 514/254.07
See application file for complete search history.

(56) References Cited

U.S. PATENT DOCUMENTS

| | | | |
|---|---|---|---|
| 7,188,993 B1 | 3/2007 | Howe et al. | |
| 9,381,518 B2 * | 7/2016 | Leung | A61K 31/192 |
| 2002/0142049 A1 | 10/2002 | Lee | |
| 2010/0270695 A1 | 10/2010 | Radosz et al. | |
| 2010/0294113 A1 | 11/2010 | McPherson | |

OTHER PUBLICATIONS

Qi, "Acoustic Nanoparticle Synthesis for Applications in Nanomedicine", Aug. 11, 2017, 15-16, 31-40.*
Jog, Pharmaceutical Sciences, 2016, vol. 106: pp. 39-65 , and Leung, U.S. Pat. No. 9,381,518.*
Sumpter, Polymer, 2003, vol. 44: pp. 4389-4403.*
Qi, Nanomedicine: Aug. 11, 2017, 31-40.*
Guo, International Journal of Pharmaceutics 592 (2021) 120026.*
Jog, R et al, Pharmaceutical Amorphous Nanoparticles, Journal of Pharmaceutical Sciences, 2016, 39-65, 106.
Oi, A et al, Acoustic Nanoparticle Synthesis for Applications i n Nanomedicine, Acoustic Nanoparticle Synthesis for Applications in Nanomedicine, 2017, 31-40.
Sumpter, B et al, Recent developments in the formation, characterization, and simulation of micron and nano-scale droplets of amorphous polymer blends and semi-crystalline polymers, Polymer, 2003, 4389-4403, 44.
International Search Report and Written Opinion for PCT/US18/047015, dated Nov. 9, 2018; 10 pages.

* cited by examiner

*Primary Examiner* — Nizal S Chandrakumar
(74) *Attorney, Agent, or Firm* — Dianne Pecoraro; John C. Todaro

(57) ABSTRACT

The present invention relates to methods for producing a stable amorphous dispersion of a pharmaceutically active substance having poor water solubility by applying low frequency acoustic energy to a mixture comprising the active substance and at least one polymer and heating the mixture until a stable amorphous dispersion is formed. The methods of the invention are an effective means of converting a crystalline API to a substantially amorphous and stable form, i.e., wherein the crystallinity is less than about 5%. The methods of the invention result in more complete amorphization, increased solubility, drug loading and stability as compared typical amorphization or literature methods.

20 Claims, 4 Drawing Sheets

METHODS FOR PREPARING STABILIZED AMORPHOUS DRUG FORMULATIONS USING ACOUSTIC FUSION

CROSS-REFERENCE TO RELATED APPLICATIONS

This application is a § 371 National Stage Application of PCT/US2018/047015, international filing date of Aug. 20, 2018, which claims the benefit of U.S. Provisional Application No. U.S. 62/550,025, filed on Aug. 25, 2017, the contents of which are hereby incorporated by reference in their entirety.

FIELD OF THE INVENTION

The present invention relates to methods for preparing stable amorphous dispersions of poorly soluble active pharmaceutical ingredients (APIs) via processing with a polymer, and compositions made thereby. The methods of the invention result in more complete amorphization, increased solubility, drug loading and stability.

BACKGROUND OF THE INVENTION

The formulation and delivery of poorly soluble drug candidates remains a challenge. One general strategy to overcome these challenges has been to stabilize the more soluble amorphous solid form of a drug with polymer and surfactant excipients, resulting in amorphous solid dispersions of drug with improved solubility and absorption in vivo. Solvent mediated techniques such as spray drying and solvent casting have emerged as options for preparing amorphous dispersions, but require that the materials used be soluble in organic solvent. Hot melt extrusion (HME) has also been established as a method for preparing amorphous dispersion of drug and polymer mixtures in the absence of solvent. However, HME requires large amounts of materials (>10 grams) and is not suitable for early formulation work in drug discovery, where the amount of material is limited.

Poor aqueous solubility can be a serious problem for achieving adequate drug bioavailability. In particular, poor solubility often limits oral absorption from the gastrointestinal (GI) tract. Drug solid state forms with optimal solubility and dissolution rates can result in better absorption from the GI tract. It follows that using a drug form with optimal solubility can also allow for similar plasma levels as seen with a larger dose of a less soluble form. Therefore, enhancing the dissolution, solubility and bioavailability of poorly soluble drugs is of great interest in the art.

In general, amorphous forms of a substance show a higher kinetic solubility and/or dissolution rate than crystalline forms of the same substance. The higher kinetic dissolution rate/solubility of amorphous phases as well as potential supersaturation can result in better bioavailability as compared to an associated crystalline form. More soluble amorphous phases are desirable for both human solid dosage forms and for use in formulations (suspensions) for preclinical toxicology studies, where large exposure margins often are required.

Frequently, amorphous drugs will convert to the lower energy crystalline phase, resulting in a drop in solubility (Hancock and Zografi, *J. Pharm Sci.* 86:1-12 (1997)). It is known that crystallization can be suppressed by dissolving the drug into an amorphous polymer, thus forming a stabilized "amorphous solid dispersion". Drug-polymer solid dispersions can be prepared via several means, including melt extrusion, solvent casting, and spray drying.

In view of the foregoing, there is a need for improving the process by which amorphous dispersion formulations are prepared, particularly for poorly organic soluble compounds and on smaller scales than those used for melt extrusion

SUMMARY OF THE INVENTION

The present invention relates to methods for preparing stable amorphous dispersions of pharmaceutically active substances with improved aqueous solubility comprising applying low frequency acoustic energy and heat to a mixture comprising an active pharmaceutical ingredient (API) and at least one polymer. The invention also provides amorphous dispersions made by the methods of the invention and compositions comprising said amorphous dispersions. The methods of the invention result in more complete amorphization, better physical stability and increased solubility and/or dissolution as compared to known solvent-free methods of preparing amorphous material. The methods of the invention are advantageous because they require a minimum amount of active pharmaceutical ingredients.

Thus, the present invention provides a method for producing a stable amorphous dispersion of a drug product comprising: (a) applying low frequency acoustic energy to a mixture comprising: (i) an API and (ii) at least one polymer; and (b) heating the mixture to a temperature above the glass transition or melting point temperatures of at least one of the polymer or the API to produce a stable amorphous dispersion of the drug product; wherein the low frequency acoustic energy and the heat are applied to the mixture for a period of time sufficient to form a stable amorphous dispersion of the drug product.

Vials of various composition, such as glass, plastic, or alloy, are loaded with drug and polymer solids in various scales, such as from 10-10,000 mg, they can be subjected to up to 100 G's of mixing intensity while being heated at various temperatures up to 200° C. It is shown herein that the methods of the invention are useful for producing amorphous dispersions of multiple compounds with different polymer systems, including Soluplus, Vit-E TPGS, PEG1500, Eudragit EPO, copovidone Kollidon® VA64, HPMCAS-LF, HPMCAS-MF, HPMCAS-HF, Kolliphor EL, and Crospovidone.

Also provided is a high throughput method of preparing multiple amorphous solid dispersion samples simultaneously, the method comprising: (a) preparing, in each chamber of a multi-chambered apparatus, a mixture comprising: (i) an active pharmaceutical ingredient; and (ii) at least one polymer; (b) applying low frequency acoustic energy to said multi-chambered apparatus; and (c) heating the apparatus to a temperature above the glass transition or melting point temperature of the mixture in each chamber of the apparatus until said amorphous solid dispersion samples are formed.

The present invention is also directed to amorphous drug product produced by the methods of the invention. In certain embodiments, the amorphous drug product contains substantially no crystalline content, preferably less than 5%, 2% or 1%.

The present invention also relates to a formulation containing the amorphous drug product in the form of a liquid suspension or a solid dosage form.

DETAILED DESCRIPTION OF THE INVENTION

Resonant acoustic mixing has emerged as a powerful method for mixing substances, including highly viscous solids. Acoustic mixers, for example, the Resodyn™ acoustic mixer (Resodyn Corporation, Butte, Mont.), are commercially available. This technology has been described, for example, by Howe et al. (U.S. Pat. No. 7,188,993), and employs linear displacement to introduce a standing linear acoustic wave into a medium, for example, a gas, liquid or solid, residing within a container affixed to the device. Preparation of admixtures comprising energetic or shock-sensitive materials has been described using acoustic mixing, for example, by McPherson, U.S. 2010/0294113. Suspension of pre-formed nanoparticulate materials in an aqueous medium has also been described, for example, the dispersion of silver nanoparticles of 20 nm-30 nm in water using an acoustic mixer (Resodyn™ marketing literature). U.S. Pat. No. 9,381,518 describes preparation of nanosuspensions by mixing an active pharmaceutical compound, an aqueous dispersion medium, and milling media and applying acoustic energy to the mixture to supply a nanosuspension having a D50 of less than about 1 micron. See also Leung, D. H., et al. *International Journal of Pharmaceutics*, 473: 10-19 (2014).

The present invention relates to use of a process, termed acoustic fusion herein, which comprises heating a mixture of active pharmaceutical ingredient and polymer solid above their glass transition or melting point temperature while conducting acoustic mixing (mixing with low frequency acoustic energy), resulting in a homogenous amorphous solid dispersion. We have demonstrated that by (a) applying low frequency acoustic energy to a mixture comprising: (i) an API and (ii) at least one polymer; and (b) heating the mixture to a temperature above the glass transition or melting point temperatures of at least one of the polymer or the API, the drug and polymer fuse to form amorphous glassy solids after a given amount of mixing time. The low frequency acoustic energy and the heat are applied to the mixture for a period of time sufficient to form a stable amorphous dispersion of the drug product, e.g. 15-30 minutes.

The solid mixtures formed by the methods of the invention are dense, glassy solids that can be converted to a solid powder through various secondary processing techniques. The glassy solids can be characterized as amorphous materials containing drug solid dispersed within the polymer matrix. As demonstrated in the Examples, amorphous anacetrapib, Vit-E TPGS, and copovidone VA64® dispersions made using the acoustic fusion process crystallized more slowly when dispersed into simulated intestinal fluid. As compared to classical amorphization processes such as spray drying, the present invention results in high efficiency and avoidance of organic solvents.

Figure 1:
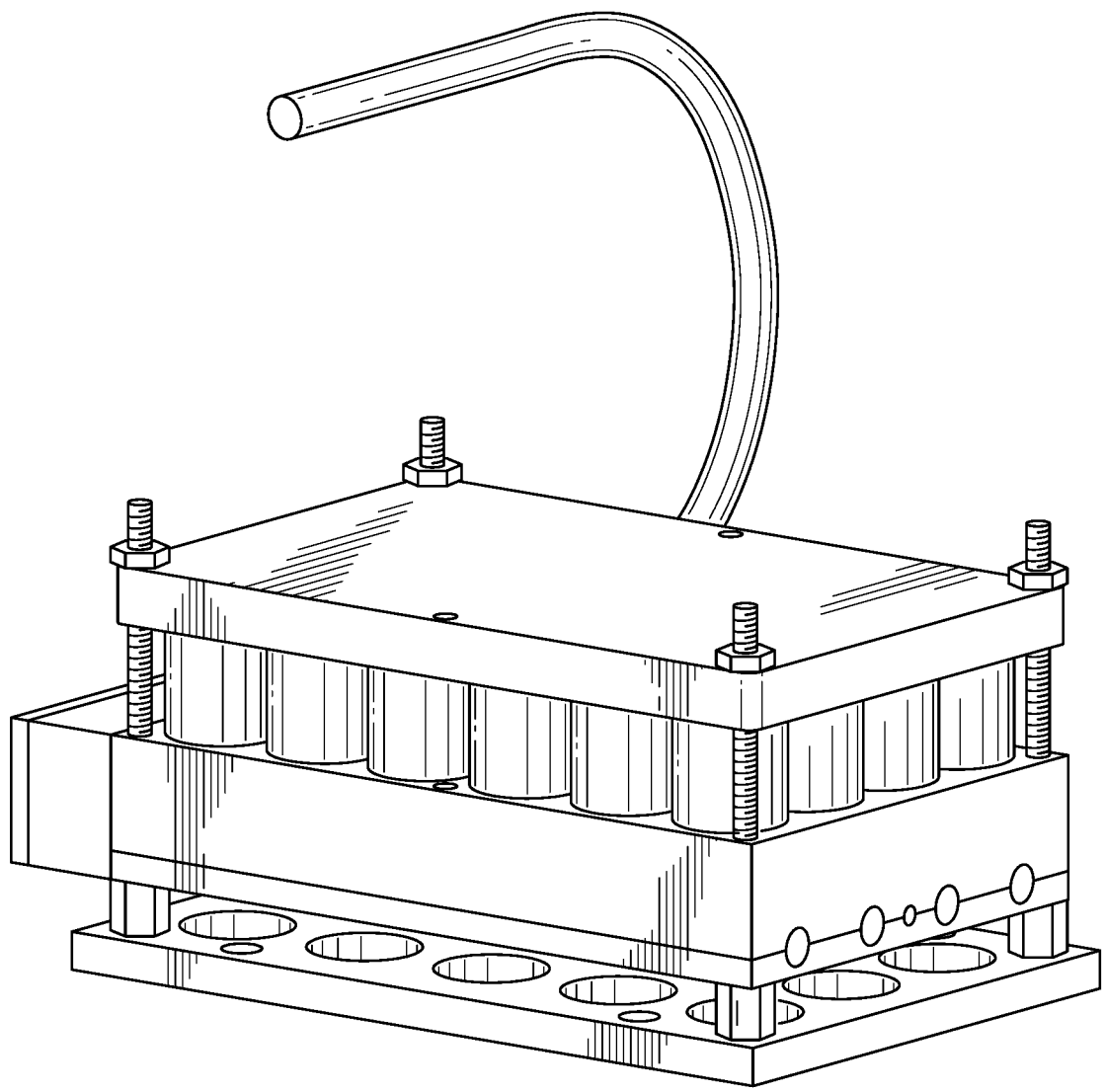
FIG. 1 shows the heating apparatus used in the acoustic fusion process. The apparatus comprises a 24-well heating block assembly that can be attached to the Resodyn Labram resonant acoustic benchtop mixer.
Figure 2:
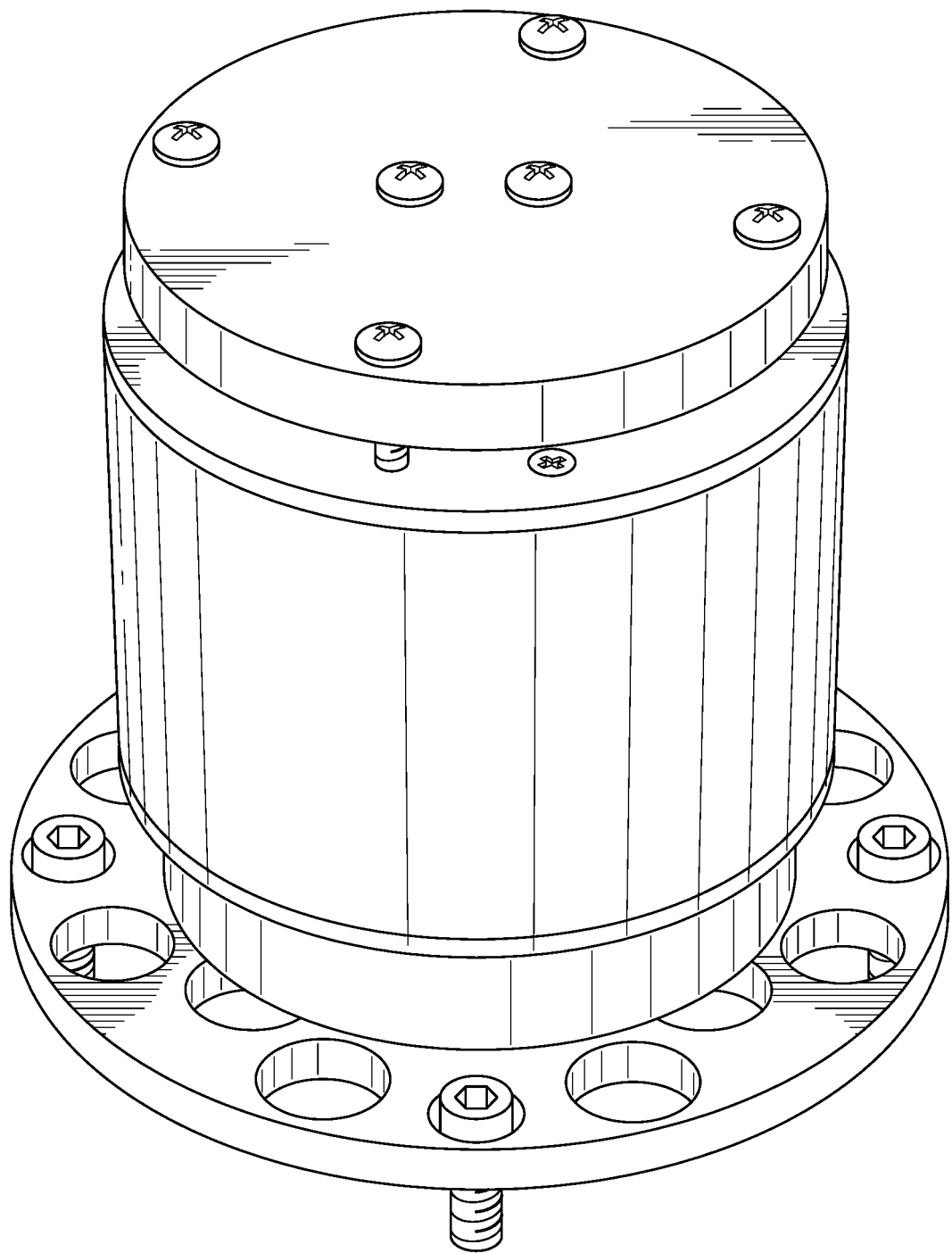
FIG. 2 shows an alternative heating apparatus that can be used in the acoustic fusion process. The apparatus comprises a 4-well heating block assembly that can be attached to the Resodyn Labram resonant acoustic benchtop mixer.

In order to enable the methods of the invention, we have designed and fabricated a 24-well heating block assembly that can be attached to the Resodyn Labram resonant acoustic benchtop mixer (FIG. 1). This heating block can be heated up to 200° C. with sufficient capacity for 24 glass vials that can be loaded with drug and polymer solid material. In another example, we also designed and fabricated a 4-well heating block assembly that can be attached to the Resodyn Labram resonant acoustic benchtop mixer (FIG. 2). This heating block can be heated up to 200° C. with sufficient capacity for up to 4 vials (the vials can be made from various materials including glass, polymer or alloy) that can be loaded with drug and polymer solid material. While the above-referenced heating block assemblies and acoustic mixers are useful for carrying out the methods of the invention, one skilled in the art will realize that any apparatus(es) that are capable of providing heat and acoustic energy to the sample mixtures comprising API and polymer can be used and/or fabricated.

In one embodiment, the present invention is a method for preparing an amorphous dispersions of a drug product comprising: (a) applying low frequency acoustic energy to a mixture comprising: (i) at least one active pharmaceutical compound and (ii) at least one polymer; and (b) heating the mixture to a temperature above the glass transition or melting point temperature of the mixture, wherein the low frequency acoustic energy and the heat are applied for a period sufficient to form a stable homogeneous amorphous solid dispersion, and wherein the final drug product has a crystalline content of about less than 5%. In specific embodiments, the acoustic energy has a frequency of from about 10 Hertz to about 1000 Hertz. In some embodiments, the acoustic energy is a standing wave supplying a linear acceleration of from about 10 G's to about 100 G's (where "G" is the force of gravity).

The methods of the invention are useful for producing an amorphous drug product with a chemical purity via chromatographic analysis of at least 95%, 98% or 99%, and which is substantially free of any crystalline material, i.e., contains less than about 5%, or 2% or 1% crystalline material.

The resulting fused glassy solids are stabilized amorphous dispersions. These formulations exhibit substantially enhanced solubility of the drug compared to the original crystalline form of the drug, which is highly desirable for drug absorption in vivo. This supersaturated solubility is prolonged due to the presence of the polymer excipient, which inhibits precipitation of and crystallization of the dissolved drug. An example of the improved kinetic solubility profile of Compound D is shown in Example 6, Table 3. In addition, formulations using model drug BCS Class 2 Torcetrapib in either Soluplus, Vit-E TPGS and copovidone Kollidon® VA64, or HPMCAS-LF were found to have improved in vitro supersaturation solubility in aqueous media compared to the crystalline free drug material, suggesting that the compound was incorporated as amorphous material in the formulations. The formulations were also tested in vivo in a rat pharmacokinetic study at a dose of 10 mg/kg. Improved absorption of up to 8-fold great exposures were observed with these formulation compared to a suspension of the crystalline material, validating the capability of these formulations for improving bioperformance.

I. Definitions and Abbreviations

As used throughout the specification and appended claims, the following abbreviations apply:
API active pharmaceutical ingredient, also referred to herein as pharmaceutically active substance
DSC differential scanning calorimetry FaSSIF fasted simulated intestinal fluid
HME hot melt extrusion
XRD X-ray diffraction So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used throughout the specification and in the appended claims, the singular forms "a," "an," and "the" include the plural reference unless the context clearly dictates otherwise.

Reference to "or" indicates either or both possibilities unless the context clearly dictates one of the indicated possibilities. In some cases, "and/or" was employed to highlight either or both possibilities.

As the term is used herein, the term "acoustic energy" means linear or spherical energy propagation through a tangible medium which is within the frequency range of 10 Hertz to 20,000 Hertz. In some embodiments of the process of the present invention, it is preferred to employ linear acoustic energy at a frequency of from about 10 Hertz up to about 100 Hertz, more preferably at a frequency of about 60 Hertz. It will be appreciated that in processes of the invention, in accordance with known principles, the exact frequency will be selected to provide a standing wave in the efficient mixing of an active pharmaceutical compound and a polymer. The frequency required to achieve a standing wave will vary according to known principles depending upon the nature of the active pharmaceutical compound and the polymer, and the dimensions of the vessel to which acoustic energy is applied.

As used herein, the term "amorphous" means a solid body devoid of long-range crystalline order. Such a lack of crystalline order can be detected and monitored. e.g., by X-ray diffraction (XRD), FT-Raman spectroscopy, polarized light microscopy (PLM) and differential scanning calorimetry (DSC).

As used herein, the phrase "substantially amorphous form" means the form contained in the amorphous solid solution is in the amorphous state, e.g., there is a minimum of 95% of active ingredient in the amorphous state in the amorphous solid solution, preferably 98% and more preferably 99% of the active ingredient, or most preferably 100% in the amorphous state. The phrase "amorphous active ingredient" is also intended to mean a non-crystalline active pharmaceutical ingredient.

An "amorphous dispersion" of a drug product is a substantially homogenous mixture of a drug product that is dispersed into a polymer which has substantially no crystalline content. A "stable amorphous dispersion" of a drug product is an amorphous dispersion containing a drug whose structure and properties remain (i.e. retains its physical stability and/or chemical stability) or can be caused to remain essentially unchanged for a period of time sufficient to allow use of the drug for the intended purpose (e.g., use in an in vivo study in an animal model or therapeutic administration to a subject). Various analytical techniques for measuring stability are available in the art including X-ray Powder Diffraction, high performance liquid chromatography, and Differential Scanning calorimetry.

In some embodiments, a "stable" amorphous stable drug dispersion is a formulation with no significant changes observed at a refrigerated temperature (2-8° C.) for at least 3 months, or at room temperature (23-27° C.) for at least 1 month. Typical acceptable criteria for stability are as follows: No more than 10%, preferably 5%, of small molecule API is degraded as measured by HPLC. The formulation generated from the dispersions after storage, in comparison to the reference (the formulation generated from the fresh prepared amorphous dispersion), have no more than 10% change in API concentration or pH value. Potency is typically within a range of 50-150% of the reference.

As used herein, the term "milling" means grinding between two surfaces. Milling can be conducted with a mortar and pestle or a milling process such as ball milling, roller milling, or gravatory milling.

As used herein, the phrase "poorly soluble active agents" means active agents having a solubility in at least one liquid dispersion medium of less than about 30 mg/ml, preferably less than about 20 mg/ml, preferably less than about 10 mg/ml, preferably less than about 1 mg/ml, or preferably less than about 0.1 mg/ml. Such active agents tend to be eliminated from the gastrointestinal tract before being absorbed into the circulation. Moreover, poorly water soluble active agents tend to be unsafe for intravenous administration techniques, which are used primarily in conjunction with highly water soluble active agents.

The term "pharmaceutical formulation" refers to preparations which are in such form as to permit the active ingredients to be effective, and which contains no additional components which are toxic to the subjects to which the formulation would be administered.

"Pharmaceutically acceptable" refers to excipients (vehicles, additives) and compositions that can reasonably be administered to a subject to provide an effective dose of the active ingredient employed and that are "generally regarded as safe" e.g., that are physiologically tolerable and do not typically produce an allergic or similar untoward reaction, such as gastric upset and the like, when administered to a human. In another embodiment, this term refers to molecular entities and compositions approved by a regulatory agency of the federal or a state government or listed in the U.S. Pharmacopeia or another generally recognized pharmacopeia for use in animals, and more particularly in humans.

The term "pharmaceutically effective amount" or "effective amount" means an amount whereby sufficient therapeutic composition or formulation is introduced to a patient to treat a diseased or condition. One skilled in the art recognizes that this level may vary according the patient's characteristics such as age, weight, etc.

The term "about", when modifying the quantity (e.g., mg, or M) of a substance or composition, the percentage (v/v or w/v) of a formulation component, or the value of a parameter characterizing a step in a method (e.g. the temperature at which a process step is conducted, the frequency at which acoustic energy is applies to a method) or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1%, 0.5%, 1%, 2%, 3%, 4%, 5%, or 10%.

The term "patient" (alternatively referred to as "subject" or "individual" herein) refers to a mammal (e.g., rat, mouse, dog, cat, rabbit) capable of being treated with the formulations of the invention, most preferably a human. The term "patient" may also include non-human animals including livestock animals and domestic animals including, but not limited to, cattle, horses, sheep, swine, goats, rabbits, cats, dogs, and other mammals in need of treatment. In some embodiments, the patient is an adult patient. In other embodiments, the patient is a pediatric patient.

An "active pharmaceutical ingredient" or "API" (also referred to herein as an active pharmaceutical compound) is an active compound useful for inducing a desired positive therapeutic effect when administered to a patient, e.g. treating or preventing a disease or condition, which may include halting or delaying the progression of a disease or pathological condition, reducing the severity or duration of the clinical symptoms of the disease, prolonging the survival of a patient relative to the expected survival in a similar untreated patient, and inducing complete or partial remission of the disease or condition.

II. Methods of the Invention

In one aspect, the invention is related to a method for producing a stable amorphous dispersion of a drug product comprising:
(a) applying low frequency acoustic energy to a mixture comprising: (i) an active pharmaceutical ingredient (API) and (ii) at least one polymer; and
(b) heating the mixture to a temperature above the glass transition or meting point temperatures of at least one of the polymer or the API to produce a stable amorphous dispersion of the drug product;
wherein the low frequency acoustic energy and the heat are applied to the mixture for a period of time sufficient to form a stable amorphous dispersion of the drug product, and wherein the drug product has a crystalline content of about less than about 5%.

The methods of the invention, which allow the preparation of amorphous drug product dispersions without solvent, can be conducted at small scales currently not achievable with hot melt extrusion approaches. This enables the preparation of amorphous drug formulations at scales sufficient to support preclinical studies, at a minimum of only 1-2 mg of drug with an appropriate amount of polymer. As noted above, the methods of the invention do not require solvent, which alleviates concerns about residual solvent impurities, and can be used for drugs or polymers that are insoluble in organic solvent, making them incompatible with spray drying processes. Acoustic energy can be supplied to an admixture using any known source; however, in general, it is preferred to supply the energy by cyclic linear displacement of a container filled with the admixture. In processes of the invention, preferably the acoustic energy supplied by linear displacement exerts between about 10 times G-force (where "G" is the force of gravity) and about 100 times G-force. Although it will be appreciated that numerous mechanical or electronic transducer arrangements can be utilized to supply the cyclic linear displacement required to generate the desired G-force within the desired frequency range, one example of commercially available equipment suitable for supplying the necessary acoustic energy is the Resodyn™ acoustic mixer, manufactured by Resodyn Acoustic Mixers, Inc., which makes equipment available in a range of capacities from bench-scale to multi-kilogram capacity.

As mentioned above, it was previously known that an acoustic mixer such as a Resodyn™ acoustic mixer could be used to efficiently provide mixing of solid and/or liquid materials. However, acoustic mixing has not been previously employed to prepare amorphous solid dispersion from powdered solid materials. Moreover, amorphous solid dispersion products prepared with acoustic energy have unique stability and unique properties. Example of such properties provided by amorphous solid dispersion prepared in accordance with the process of the present invention include: density, dissolution rate, supersaturation profile, and longer physical stability.

The fused glassy solids resulting from the methods of the invention are stabilized amorphous dispersions. These formulations exhibit substantially enhanced solubility of the drug compared to the original crystalline form of the drug, which is highly desirable for drug absorption in vivo. This supersaturated solubility is prolonged due to the presence of the polymer excipient, which inhibits precipitation of and crystallization of the dissolved drug. An example of the improved kinetic solubility profile of Compound D (as described in Example 1, infra) is shown in Table 3 (see EXAMPLE 6).

In dissolution studies, the amorphous material produced has been shown to sustain supersaturated solubility of model drug compound B at concentrations above that of the crystalline drug solid. This demonstrates that the amorphous dispersions produced by acoustic fusion are capable of sustaining high concentrations of solubilized drug.

In vivo pharmacokinetic studies involving rat models dosed with formulations of Torcetrapib have demonstrated that the amorphous materials produced using acoustic fusion are capable of improving oral absorption of drug compounds by up to 8-fold compared to a suspension of the crystalline drug solid (see EXAMPLE 5).

As noted above, in the methods of the invention, acoustic energy is applied to an admixture comprising an API and at least one polymer. The acoustic energy should be of sufficient frequency and amplitude and for a sustained period sufficient to provide a stable homogeneous amorphous solid dispersion.

In embodiments of the invention, the low frequency acoustic energy is applied at a frequency of about 10 Hertz to about 100 Hertz. In additional embodiments, the low frequency acoustic energy is applied at a frequency of about 10 Hertz to about 90 Hertz, about 10 Hertz to about 80 Hertz, about 10 Hertz to about 75 Hertz, about 10 Hertz to about 70 Hertz, about 10 Hertz to about 60 Hertz, about 10 Hertz to about 50 Hertz, about 10 Hertz to about 40 Hertz, about 10 Hertz to about 30 Hertz, about 10 Hertz to about 20 Hertz, about 20 Hertz to about 100 Hertz, about 20 Hertz to about 90 Hertz, about 20 Hertz to about 80 Hertz, about 20 Hertz to about 75 Hertz, about 20 Hertz to about 70 Hertz, about 20 Hertz to about 60 Hertz, about 20 Hertz to about 50 Hertz, about 20 Hertz to about 40 Hertz, about 20 Hertz to about 30 Hertz, about 30 Hertz to about 100 Hertz, about 30 Hertz to about 90 Hertz, about 30 Hertz to about 80 Hertz, about 30 Hertz to about 70 Hertz, about 30 Hertz to about 60 Hertz, about 30 Hertz to about 50 Hertz, about 30 Hertz to about 40 Hertz, about 40 Hertz to about 100 Hertz, about 40 Hertz to about 90 Hertz, about 40 Hertz to about 80 Hertz, about 40 Hertz to about 70 Hertz, about 40 Hertz to about 60 Hertz, about 40 Hertz to about 50 Hertz, about 50 Hertz to about 100 Hertz, about 50 Hertz to about 90 Hertz, about 50 Hertz to about 80 Hertz, about 50 Hertz to about 75 Hertz, about 50 Hertz to about 70 Hertz, about 50 Hertz to about 60 Hertz, about 60 Hertz to about 100 Hertz, about 60 Hertz to about 90 Hertz, about 60 Hertz to about 80 Hertz, about 60 Hertz to about 70 Hertz, about 70 Hertz to about 100 Hertz, about 70 Hertz to about 90 Hertz, about 70 Hertz to about 80 Hertz, about 80 Hertz to about 100 Hertz, about 80 Hertz to about 90 Hertz, or about 90 Hertz to about 100 Hertz.

In further embodiments of the invention, the low frequency acoustic energy is applied at a frequency of about 10 Hertz, about 20 Hertz, about 30 Hertz, about 40 Hertz, about 50 Hertz, about 60 Hertz, about 70 Hertz, about 80 Hertz, about 90 Hertz, or about 100 Hertz.

In specific embodiments of the invention, the acoustic energy is applied as a standing wave.

In certain embodiments of the invention, including any of the embodiments above, the acoustic energy imparts a force of from about 10 G to about 100 G. In additional embodiments, the low frequency acoustic energy is applied at a frequency of about 10 G to about 90 G, about 10 G to about 80 G, about 10 G to about 75 G, about 10 G to about 70 G, about 10 G to about 60 G, about 10 G to about 50 G, about 10 G to about 40 G, about 10 G to about 30 G, about 10 G to about 20 G, about 20 G to about 100 G, about 20 G to about 90 G, about 20 G to about 80 G, about 20 G to about 75 G, about 20 G to about 70 G, about 20 G to about 60 G, about 20 G to about 50 G, about 20 G to about 40 G, about 20 G to about 30 G, about 30 G to about 100 G, about 30 G to about 90 G, about 30 G to about 80 G, about 30 G to about 70 G, about 30 G to about 60 G, about 30 G to about 50 G, about 30 G to about 40 G, about 40 G to about 100 G, about 40 G to about 90 G, about 40 G to about 80 G, about 40 G to about 70 G, about 40 G to about 60 G, about 40 G to about 50 G, about 50 G to about 100 G, about 50 G to about 90 G, about 50 G to about 80 G, about 50 G to about 75 G, about 50 G to about 70 G, about 50 G to about 60 G, about 60 G to about 100 G, about 60 G to about 90 G, about 60 G to about 80 G, about 60 G to about 70 G, about 70 G to about 100 G, about 70 G to about 90 G, about 70 G to about 80 G, about 80 G to about 100 G, about 80 G to about 90 G, or about 90 G to about 100 G.

In further embodiments of the invention, the acoustic energy imparts a force of about 10 G, about 20 G, about 30 G, about 40 G, about 50 G, about 60 G, about 70 G, about 80 G, about 90 G, or about 100 G.

Polymers

The invention provides methods for producing a stable amorphous dispersion of a drug product from an admixture of at least one API and at least one polymer. The addition of an amorphous polymer to a mixture comprising an API serves to aid in amorphization and increase solubility. Without being bound by any mechanism, the increased solubility may be due in part to suppression of seed crystal formation which would lead to crystallization. Polymers useful in the methods of the invention include, but are not limited to cellulosic polymers and vinyl homopolymers and copolymers.

In certain embodiments, the polymer is a cellulose, acrylate, poloxamer, vinyl homopolymer or copolymer, polyethylene glycol, aminosaccharide or polyethylene oxide.

In other embodiments, the polymer is selected from the group consisting of: Hydroxypropyl Methylcellulose Acetate Succinate (HPMCAS-LF, HPMCAS-MF, HPMCAS-HF), Vitamin E TPGS, Polyethylene Glycol, methacrylate copolymer, copovidone, Polyoxyl 35 hydrogenated castor oil, polyvinyl caprolactam-polyvinyl acetate-polyethylene glycol grafted copolymer, and Polyvinylpyrrolidone.

Examples of cellulose (cellulosic polymers), which can be modified with one or more hydrophobic/hydrophilic groups (e.g., a carboxylic acid) or a methacrylic acid copolymer, include, but are not limited to alkylcelluloses, e.g., methylcellulose; hydroxyalkylcelluloses, e.g., hydroxymethylcellulose, hydroxyethylcellulose (Natrosol™, Ashland, Covington, Ky.), hydroxypropylcellulose, hydroxybutylcellulose and weakly substituted hydroxypropylcellulose; hydroxyalkylalkylcelluloses, e.g., ethyl(hydroxyethyl)cellulose, hydroxyethylmethylcellulose and hydroxypropylmethylcellulose (e.g., Methocel™, types A, E, K, F, Dow Wolff Cellulosics GmbH, Bomlitz, Germany); carboxyalkylcelluloses, e.g., carboxymethylcellulose; carboxyalkylcellulose salts, e.g., sodium carboxymethylcellulose; carboxyalkylalkylcelluloses, e.g., carboxymethylethylcellulose; esters of cellulose derivatives, e.g., hydroxypropylmethylcellulose phthalate, hydroxypropylmethylcellulose acetate succinate (e.g., AQOAT® (Shin-Etsu, Tokyo, Japan)), and cellulose acetate phthalate-hydroxypropylcellulose (e.g., KLUCEL® (Ashland, Covington, Ky.)).

Examples of acrylate include polyacrylates including, but are not limited to, methacrylic acid copolymer, polymethacrylates (Eudragit® L-100-55 and Eudragit® E-100, Evonik Degussa Corporation, Parsipanny, N.J.), polyacrylic acid (Carbopol®, The Lubrizol Corporation, Wickliffe, Ohio).

Examples of vinyl homopolymers and copolymers include, but are not limited to, polymers of N-vinylpyrrolidone, in particular povidone, copovidone, polyvinyl alcohol, and polyvinylpyrrolidone (Kollidon™, PVP and PVP-VA, BASF SE, Ludwigshafen, Germany).

Examples of other types of synthetic polymers include, but are not limited to, polyethylene oxide (Polyox™, Dow Chemical Company, Midland, Mich.), polyethyleneglycols of various molecular weights, polyethylene-/polypropylene-/polyethylene-oxide block copolymers and natural gums and polysaccharides-Xanthan gum (Keltrol™, CP Kelco, Atlanta, Ga.), carrageenan, locust bean gum, acacia gum, chitosan, alginic acid, hyaluronic acid, pectin, etc. Suitable polyethyleneglycols are especially Polyethyleneglycol 8000 and Polyethyleneglycol 6000. A suitable polyethylene-/polypropylene-/polyethylene-oxide block copolymer is in particular Pluronic F68.

Secondary Polymers and Copolymers, and Plasticizers and Surfactants.

A secondary polymer, which serves to aid in amorphization and increase solubility, can also be added to the admixture of API and polymer, as noted above, in the methods of the invention. Thus, one aspect of the invention relates to a method of producing a stable amorphous dispersion of a drug product comprising: (a) applying low frequency acoustic energy to a mixture comprising: (i) an active pharmaceutical ingredient (API) (ii) a first polymer; and (iii) a secondary polymer; and (b) heating the mixture to a temperature above the glass transition or melting point temperatures of at least one of the components of the mixture (API, first polymer or second polymer) to produce a stable amorphous dispersion of the drug product. In the methods of the invention, steps (a) and (b) are carried out until the mixture is substantially free of any crystalline material. Without being bound by any mechanism, the increased solubility may be due in part to suppression of seed crystal formation which would lead to crystallization. Secondary polymers useful in the methods of the invention include, but are not limited to cellulosic polymers and vinyl homopolymers and copolymers.

Any polymer useful in the methods of the invention can be used as a secondary polymer, i.e. mixtures of more than one polymer described above in the mixture are contemplated. In one embodiment of the method above, the secondary polymer is selected from the group consisting of: cellulose, acrylate, poloxamer, vinyl homopolymer or copolymer, polyethylene glycol, aminosaccharide and polyethylene oxide.

In one aspect, the secondary polymer is hydroxypropyl methylcellulose functionalized with a carboxylic acid (e.g., hydroxypropyl methylcellulose succinate or hydroxypropyl methylcellulose phthalate).

In additional embodiments, the mixture of API and polymer (with or without secondary polymer) further comprises a plasticizer and/or surfactant. Plasticizers and surfactants useful in the methods of the invention include, but are not limited to: glycerol, propylene glycol, PEG 200-6000, triacetin, diethyl phthalate, dibutyl phthalate, tributyl citrate, Castrol oil, Vitamin-E TPGS, polysorbate 20 (e.g. Tween 20) and polysorbate 80 (e.g. Tween 80).

Drugs/API

Active pharmaceutical ingredients useful in the methods of the present invention include all compounds known to be useful for treating patients, preferably those compounds that also have low water solubility, e.g., less than 50 µg/ml. Such compounds include all compounds categorized as Class II (compounds with high permeability and low solubility) or Class IV (compounds with low permeability and low solubility) under the Biopharmaceutical Classification System (BCS) of the United States Food and Drug Administration (FDA). See *Waiver of In Vivo Bioavailability and Bioequivalence Studies for Immediate Release Solid Oral Dosage Forms Based on a Biopharmaceutics Classification System, Guidance for Industry*, U.S. Department of Health and Human Services, Food and Drug Administration, Center for Drug Evaluation and Research (CDER) published August, 2000.

Thus, in certain embodiments of the invention, the API is a Class II compound. In alternative embodiments, the API is a Class IV compound.

Examples of APIs suitable for use with the methods of the invention include, but are not limited to, megestrol acetate, ciprofloxan, itroconazole, lovastatin, simvastatin, omeprazole, phenytoin, ciprofloxacin, cyclosporine, ritonavir, lopinavir, carbamazepine, carvendilol, clarithromycin, diclofenac, etoposide, budesnonide, progesterone, megestrol acetate, topiramate, naproxen, flurbiprofen, ketoprofen, desipramine, diclofenac, itraconazole, piroxicam, carbamazepine, phenytoin, verapamil, indinavir sulfate, lamivudine, stavudine, nelfinavir mesylate, a combination of lamivudine and zidovudine, saquinavir mesylate, ritonavir, zidovudine, didanosine, nevirapine, ganciclovir, zalcitabine, fluoexetine hydrochloride, sertraline hydrochloride, paroxetine hydrochloride, bupropion hydrochloride, nefazodone hydrochloride, mirtazpine, auroix, mianserin hydrochloride, zanamivir, olanzapine, risperidone, quetiapine fumurate, buspirone hydrochloride, alprazolam, lorazepam, leotan, clorazepate dipotassium, clozapine, sulpiride, amisulpride, methylphenidate hydrochloride, and pemoline.

In other embodiments, the API is megestrol acetate, ciprofloxan, itroconazole, lovastatin, simvastatin, omeprazole, phenytoin, ciprofloxacin, cyclosporine, ritonavir, lopinavir, carbamazepine, carvendilol, clarithromycin, diclofenac, etoposide, budesnonide, progesterone, megestrol acetate, topiramate, naproxen, flurbiprofen, ketoprofen, desipramine, diclofenac, itraconazole, piroxicam, carbamazepine, phenytoin, and verapamil. In additional embodiments, the API is megestrol acetate, ciprofloxan, itroconazole, lovastatin, simvastatin, omeprazole, phenytoin, ciprofloxacin, cyclosporine, ritonavir, carbamazepine, carvendilol, clarithromycin, diclofenac, etoposide, or budesnonide.

In specific embodiments of the methods of the invention, the API is anacetrapib, posaconazole, itraconazole, or lopinavir.

In a specific embodiment of the invention, the API is posaconazole or itraconazole.

In other embodiments, the API is Lopinavir or ($\alpha$S)—N-[(1S,3S,4S)-4-[[2-(2,6-Dimethylphenoxy)acetyl]amino]-3-hydroxy-5-phenyl-1-(phenylmethyl)pentyl]tetrahydro-$\alpha$-(1-methylethyl)-2-oxo-1(2H)-pyrimidineacetamide.

In further embodiments, the API is Torcetrapib or (2R,4S)-4-[(3,5-Bis-trifluoromethylbenzyl)methoxycarbonylamino]-2-ethyl-6-trifluoromethyl-3,4-dihydro-2H-quinoline-1-carboxylic acid ethyl ester.

In any of the embodiments of the methods of the invention, the API is present (i.e. drug load) in a range from about 1% to about 75% by weight. In other embodiments, the API is present in a range from about 10% to about 50% by weight, or about 20% to about 40% by weight. In further embodiments, the drug load of the API in the mixture is about 5%, about 5%, about 10%, about 15%, about 20%, about 25%, about 30%, about 35%, about 40%, about 45%, about 50%, about 55%, about 60%, about 65%, about 70%, or about 75. In still further embodiments, the drug load of the API is about 23%, about 33%, or about 20 to about 33%.

The methods of the invention are useful for producing amorphous stable drug product dispersions wherein the drug product contains substantially no crystalline content. In some embodiments, the drug product produced by the methods of the invention has a crystalline content of about less than 5%, about less than 4%, about less than 3%, about less than 2%, or about less than 1%.

The invention also relates to amorphous stable drug products prepared in accordance with the methods of the invention. The invention is further related to a pharmaceutical formulation comprising an amorphous stable drug product prepared in accordance with the methods of the invention, together with a pharmaceutically acceptable carrier. In embodiments of this aspect of the invention, the formulation is in the form of a liquid suspension or a solid dosage form.

Drug Product Processing

After the acoustic fusion process, a dense, glassy solid is formed typically as a single mass. Removal of the glassy solid from the glass vial container can be facilitated, e.g., by pre-coating the vial with magnesium stearate or other lubricant or by the use of silanized glass vials. The glassy material can be processed into powder using a mortar and pestle or other typical grinding techniques.

The solid solution thus obtained by one of the processes according to the invention can be milled so as to obtain a fine powder (i.e. particle size<300 µm).

Thus, in additional embodiments of the invention, there is provided a method for producing a stable amorphous dispersion of a drug product as described above, wherein the method further comprises the step of processing the stable amorphous dispersion into a powder using a grinding technique.

In a specific embodiments of the invention, the drug product is milled after the stable amorphous dispersion is formed.

High Throughput Method

The invention also provides a process for preparing multiple amorphous solid dispersion samples simultaneously, the method comprising: (a) loading, into two or more chambers of a multi-chambered apparatus, a mixture comprising: (i) an active pharmaceutical ingredient; and (ii) at least one polymer; (b) applying low frequency acoustic energy to said multi-chambered apparatus; and (c) heating the apparatus to a temperature above the glass transition or melting point temperature of the mixture in each chamber of the apparatus until said amorphous solid dispersion samples are formed.

It is understood that in order to allow the formation of multiple amorphous dispersions simultaneously, a temperature should be selected that is above the highest glass transition or melting point temperature of each of the mixtures that is loaded into the apparatus. Likewise, acoustic energy should be applied at a frequency and for a period of time that is sufficient to allow formation of the amorphous dispersions for each of the mixtures loaded into the apparatus.

In certain embodiments of this aspect of the invention, said low frequency acoustic energy is applied at a frequency of about 10 Hertz to about 100 Hertz. In further embodiments, the low frequency acoustic energy is applied at a frequency of about 40 Hertz to about 80 Hertz, about 50 Hertz to about 70 Hertz, or about 60 Hertz.

In some embodiments, the acoustic energy imparts a force of from about 10 G to about 100 G. In additional embodiments, the acoustic energy imparts a force of about 10 G, about 20 G, about 30 G, about 40 G, about 50 G, about 60 G, about 70 G, about 80 G, about 90 G, or about 100 G.

In some embodiments of this aspect of the invention, the acoustic energy is applied as a standing wave.

The methods above are useful for producing multiple amorphous stable drug product dispersions simultaneously, wherein each of the drug products contains substantially no crystalline content. In some embodiments, each of the drug products has a crystalline content of about less than 5%, about less than 4%, about less than 3%, about less than 2%, or about less than 1%.

This approach enables the high throughput evaluation of multiple drug-polymer mixtures in parallel using a multiple chamber heating block (e.g. a 24-well heating block). Multiple formulation compositions can be evaluated in parallel in order to rapidly identify the optimal amorphous dispersion formulation. We have evaluated a number of API's and polymers using the acoustic fusion approach, which produced amorphous material.

General Procedures

As a general procedure, the acoustic heating block attached to a Labram resonant acoustic mixer was preheated to 80-160° C. At the lower limit, a 4-mL glass vial was charged with drug solid (2 mg) with polymer solid (8 mg) at a total solids loading of 10 mg. The sample quantity for each vial should not exceed more than approximately 80% of the volume of the vials depending upon the bulk density of the powders. The vial was capped and then placed in the acoustic fusion heating block and clamped down. The sample was then mixed at 50-80 G's intensity for 30 minutes. The heating/mixing time can vary from 15-60 minutes; however, most drug samples achieve amorphization within 30 minutes. Afterwards, the sample was removed and cooled to room temperature. The resulting solid forms a dense, glassy solid.

Scale

Using the general procedure, the amount of total solid that can be fused can range from 10 mg to 2 g, with the upper limit dependent on the powder density of the initial solids and the 4-mL volume limitation of the sample vials. With the heating block with 20 mL glass or alloy vials, the amount of total solid that can be fused can range from 100 mg to 10 g.

Formulation

The drug/polymer dispersions can be formulated into any type of liquid or solid or semi-solid dosage form for administration by various routes, including oral, intraperitoneal or subcutaneous routes. Liquid preparations suitable for oral administration (e.g., suspensions, syrups, elixirs and the like) can be prepared according to techniques known in the art and can employ the usual media such as water, glycols, oils, alcohols and the like. For example, the dispersion can be simply suspended in an aqueous vehicle, with a typical excipient additive (e.g., 0.5% microcrystalline cellulose) as a suspending agent. Excipients that prevent agglomeration (e.g., poloxamer) also may be added. This type of formulation is especially appropriate for oral dosing in pre-clinical species (e.g., rats or mice). Solid preparations suitable for oral administration (e.g., powders, pills, capsules and tablets) can be prepared according to techniques known in the art and can employ such solid excipients as starches, sugars, kaolin, diluents, lubricants, binders, disintegrating agents and the like. Further description of methods suitable for use in preparing pharmaceutical compositions of the present invention and of ingredients suitable for use in said compositions is provided in *Remington's Pharmaceutical Sciences*, 20$^{th}$ edition, edited by A. R. Gennaro, Mack Publishing Co., 2000.

Measurements

The amount of amorphous material in a sample of milled powder can be assessed in a number of ways. Differential Scanning calorimetry (DSC) will show the heat of crystallization in a sample containing amorphous material. DSC measurements can be carried out using a TA Instruments DSC Q2000 system. The sample is weighed into the measuring pan and held at a temperature below the recrystallization temperature for 30 minutes under a flow of dry nitrogen to remove any surface moisture. The sample was then heated at a constant rate of 20° C. per minute. The exothermic peak due to recrystallization is measured. As above the method is calibrated using samples of known amorphous content.

X-ray Powder Diffraction can be carried out using a Bruker D8 Advance A25 system. The samples were exposed to CuKα radiation as the X-ray source and scanned from 4 to 40° at a step scan mode of 0.06°/s. The operating voltage was 45 kV and current was 40 mA. The equipment is calibrated with samples of known amorphous content produced by mixing fully crystalline and fully amorphous materials.

All publications mentioned herein are incorporated by reference for the purpose of describing and disclosing methodologies and materials that might be used in connection with the present invention.

Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

Example 1

Model Drugs Evaluated Using the Acoustic Fusion Method

We tested a number of model drugs using the acoustic fusion methods, as described infra. The drugs tested are representative BCS Class 2 and Class 4 drugs. The BCS (Biopharmaceutics Classification System) designation is used to group compounds into classes based on their solubility and permeability (BCS guidance "Waiver of In vivo Bioavailability and Bioequivalence Studies for Immediate Release Solid Oral Dosage Forms Based on a Biopharmaceutics Classification System," U.S. Department of Health and Human Services, Food and Drug Administration):

BCS Class 1 describes compounds with high permeability and high solubility.

BCS Class 2 describes compounds with high permeability and low solubility.

BCS Class 3 describes compounds with low permeability and high solubility.

BCS Class 4 describes compounds with low permeability and low solubility.

Under the BCS Classification System, a drug is considered highly soluble if fully solubilized in 250 mL water at the highest therapeutic dose at any physiological pH. A drug is considered highly permeable if the extent of oral absorption is greater than 90%.

Drugs tested include the following: Compound A, which is a BCS Class 2 compound investigated for the treatment of hypoglycemia (melting point 136° C., Log D 3.8), Compound B, which is a BCS Class 2 compound investigated for oncology (melting point 108° C., Log D 4.4), Compound C which is a BCS Class 2 compound investigated for the treatment of migraine (melting point 175° C., log D 2.4), Compound D, which is a BCS Class 4 compound investigated for the treatment of HCV viral infections (melting point 132° C., log D 2.9).

Also tested were the following compounds:
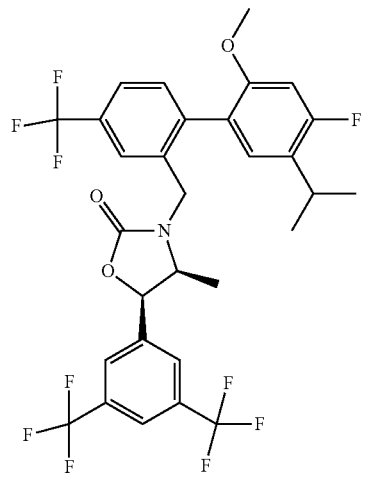
Anacetrapib, BCS Class 4
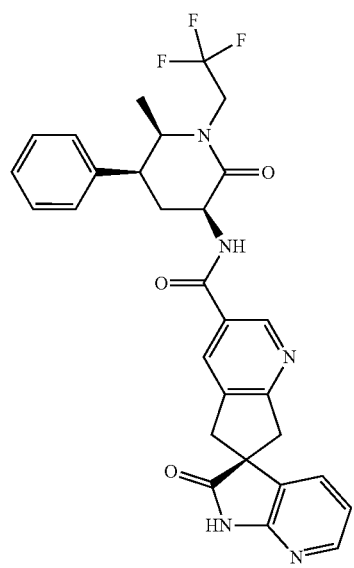
Ubrogepant, BCS Class 4
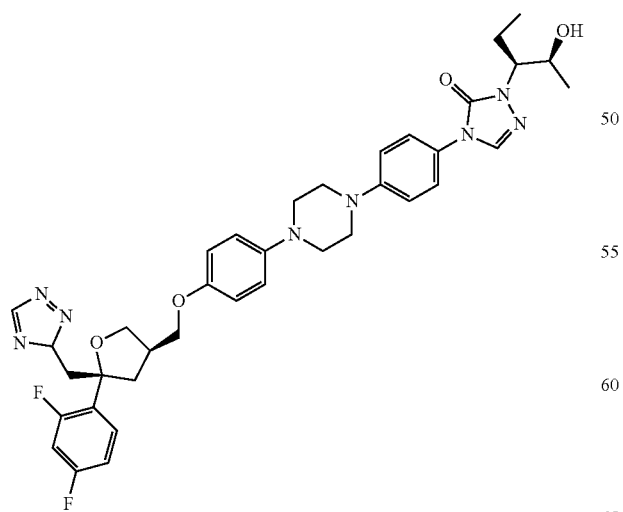
Posaconazole, BCS Class 2
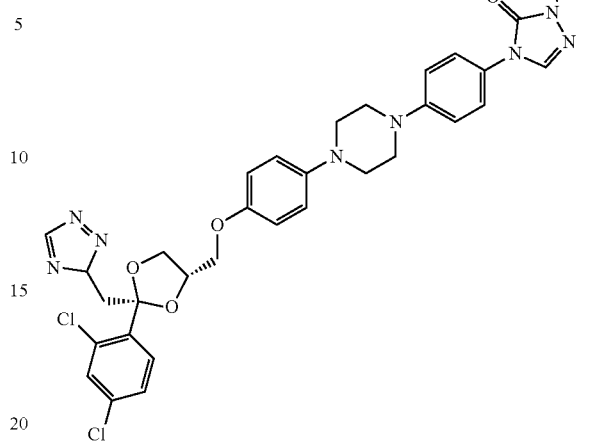
Itraconazole, BCS Class 2
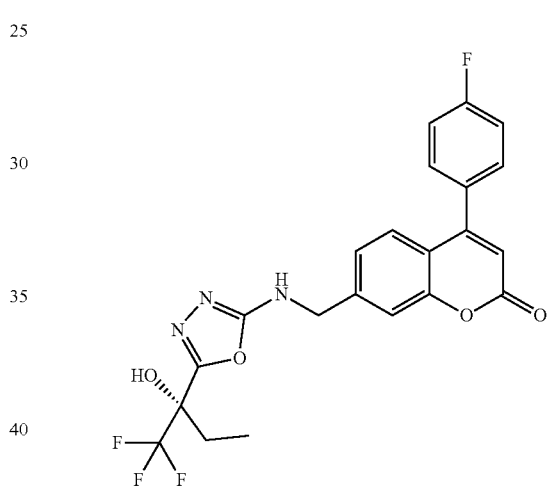
Setileuton, BCS Class 2
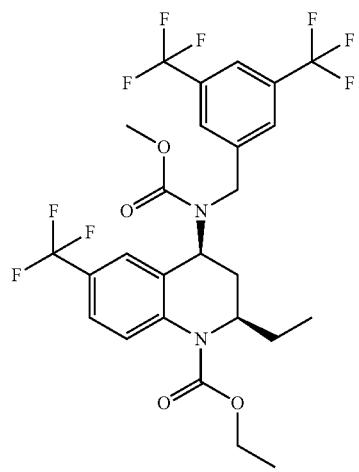
Torcetrapib, BCS Class 2

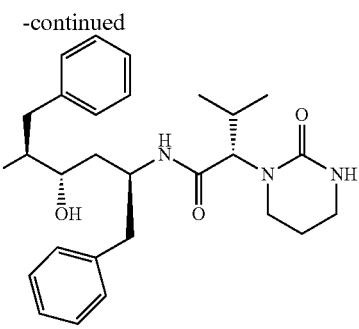

Lopinavir, BCS Class 2

The model drugs above were evaluated by mixing a drug load of between 20 and 40% with several different polymer systems as shown in Table 1 below.

The acoustic fusion process led to fused glassy solids which were stabilized amorphous dispersions for each of the systems tested in Table 1, suggesting that acoustic fusion may be useful as a general method for formulating poorly soluble drugs and allowing the production of amorphous dispersions.

TABLE 1

Model drug and polymer excipient systems successfully evaluated using the acoustic fusion method.

| Model Drug Name | Drug Load | Polymer and Surfactant Excipients Load |
|---|---|---|
| Anacetrapib | 20.0% | 70% copovidone + 10% Vit-E TPGS |
| Ubrogepant | 20.0% | 75% copovidone + 5% Vit-E TPGS |
| Setileuton | 20.0% | 68% copovidone + 10% Crospovidone + 2% Sucrose |
| Posaconazole | 25.0% | 75% HPMCAS-M |
| Itraconazole | 20% | 1) 80% HPMCAS-L<br>2) 70% copovidone + 10% Vit-E TPGS<br>3) 70% copovidone + 10% PEG1500<br>4) 70% Soluplus + 10% PEG1500 |
| Torcetrapib | 20% | 1) 80% HPMCAS-L<br>2) 70% copovidone + 10% Vit-E TPGS<br>3) 80% Soluplus |
| Lopinavir | 20% | 80% copovidone |
| Compound A | 20.0% | 80% HPMCAS-H or -L or copovidone |
| Compound B | 40.0% | 50% HPMCAS-L + 10% Cremophor EL |
| Compound C | 23.0% | 72% copovidone + 5% Vit-E TPGS |
| Compound D | 20-33% | 1) 67-80% HPMCAS-L<br>2) 80% Soluplus<br>3) 70% Soluplus + 10% PEG1500<br>4) 70% copovidone + 10% Vit-E TPGS<br>5) 70% copovidone + 10% PEG1500<br>6) 80% Eudragit EPO |

Example 2

Analytical Measurements

Determination of the amount of amorphous material in the samples described throughout the Examples was carried out using differential scanning calorimetry (DSC) and X-ray diffraction. Following processing using the acoustic fusion methods described, the samples were milled into powder prior to testing. The crystalline content detection limit of the equipment used for the studies is less than 5%.

Differential Scanning Calorimetry

DSC was used to determine the heat of crystallization in a sample containing amorphous material. DSC measurements were carried out using a TA Instruments DSC Q2000 system. Samples were weighed into the measuring pan of the DSC Q2000 system and held at a temperature below the recrystallization temperature for 30 minutes under a flow of dry nitrogen to remove any surface moisture. The samples were then heated at a constant rate of 20° C. per minute. The exothermic peak due to recrystallization was measured. The equipment was calibrated with samples of known amorphous content produced by mixing fully crystalline and fully amorphous materials.

X-Ray Diffraction

X-ray powder diffraction was carried out using a Bruker D8 Advance A25 system. The samples were exposed to CuKα radiation as the X-ray source and scanned from 4 to 40° C. at a step scan mode of 0.06°/s. The operating voltage was 45 kV and current was 40 mA. As above, the equipment was calibrated with samples of known amorphous content produced by mixing fully crystalline and fully amorphous materials.

Example 3

Acoustic Mixing of Different Amounts of Lopinavir with Copovidone VA64

Lopinavir (BCS class 2) was purchased from Acros Organics (Thermo Fisher Scientific, Waltham, Mass.). Copovidone polymer Kollidon® VA64 was purchased from BASF (BASF Corp., Florham Park, N.J.). In a first study, a mixture of 41 mg of Lopinavir and 162 mg of copovidone, were weighed into a 4-mL glass vial at an approximate drug loading of 20%. The vial was placed in a 24-well heating block element bolted onto the top of a Labram mixer (see FIG. 1). The heating block was set to 140° C. and the sample was mixed at 50% intensity/~56 G's for 30 minutes before being removed and cooled on the benchtop. The sample was then tested using DSC and X-ray diffraction as described in Example 2.

In a second study, 401 mg of compound Lopinavir, and 1602 mg of VA 64 were weighed into a 20-mL alloy vial at an approximate drug loading of 20%. The vial was placed in a 4-well heating block element bolted onto the top of a Labram mixer (see FIG. 2). The heating block was set to 140° C. and the sample was mixed at 50% intensity/~56 G's for 30 minutes before being removed and cooled on the benchtop.

Figure 3:
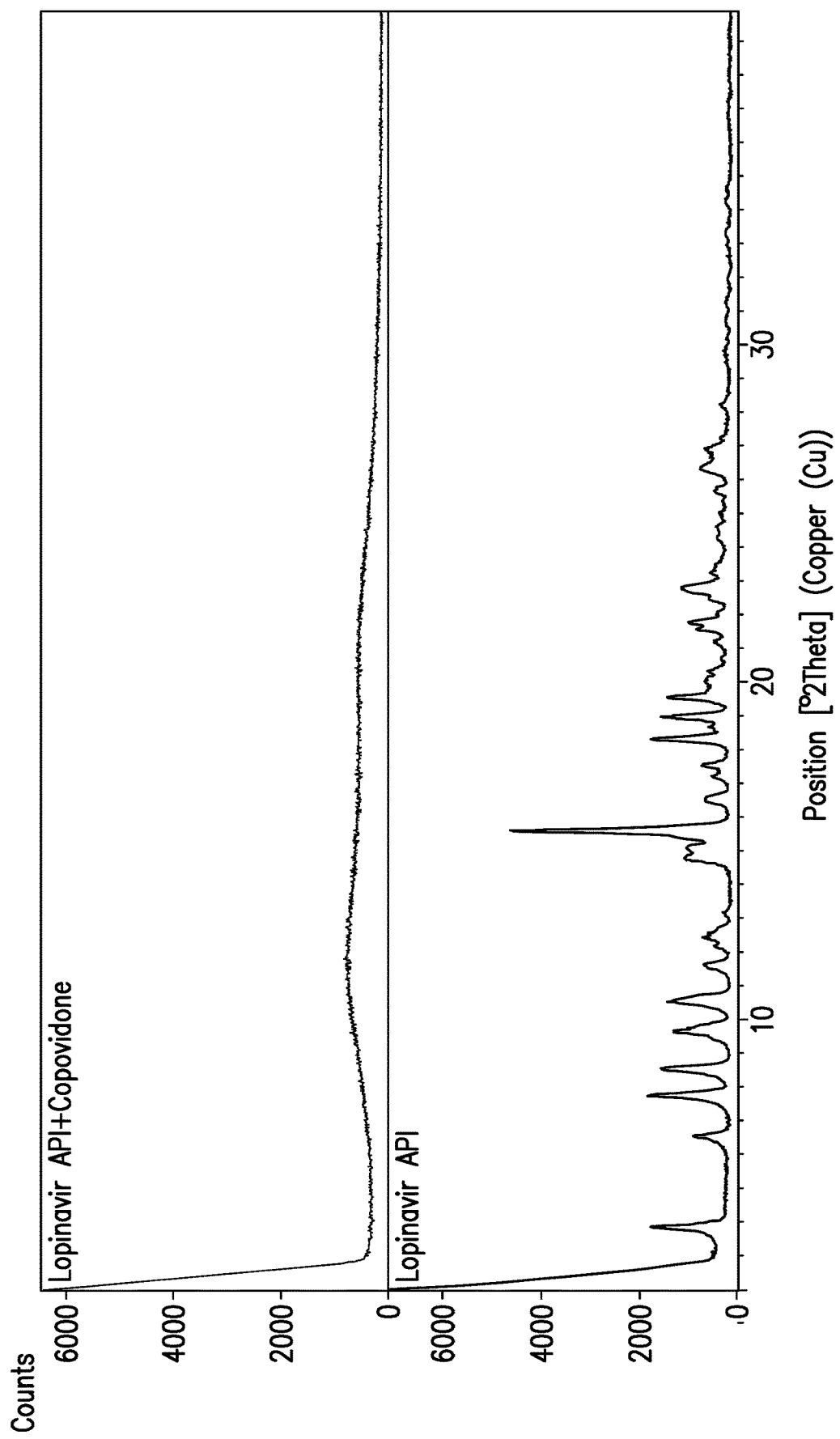
FIG. 3 shows an X-ray powder diffraction spectra for the acoustic fusion product of Lopinavir and copovidone Kollido®VA64 with approximate drug loading of 20% (see Example 3).
Figure 4:
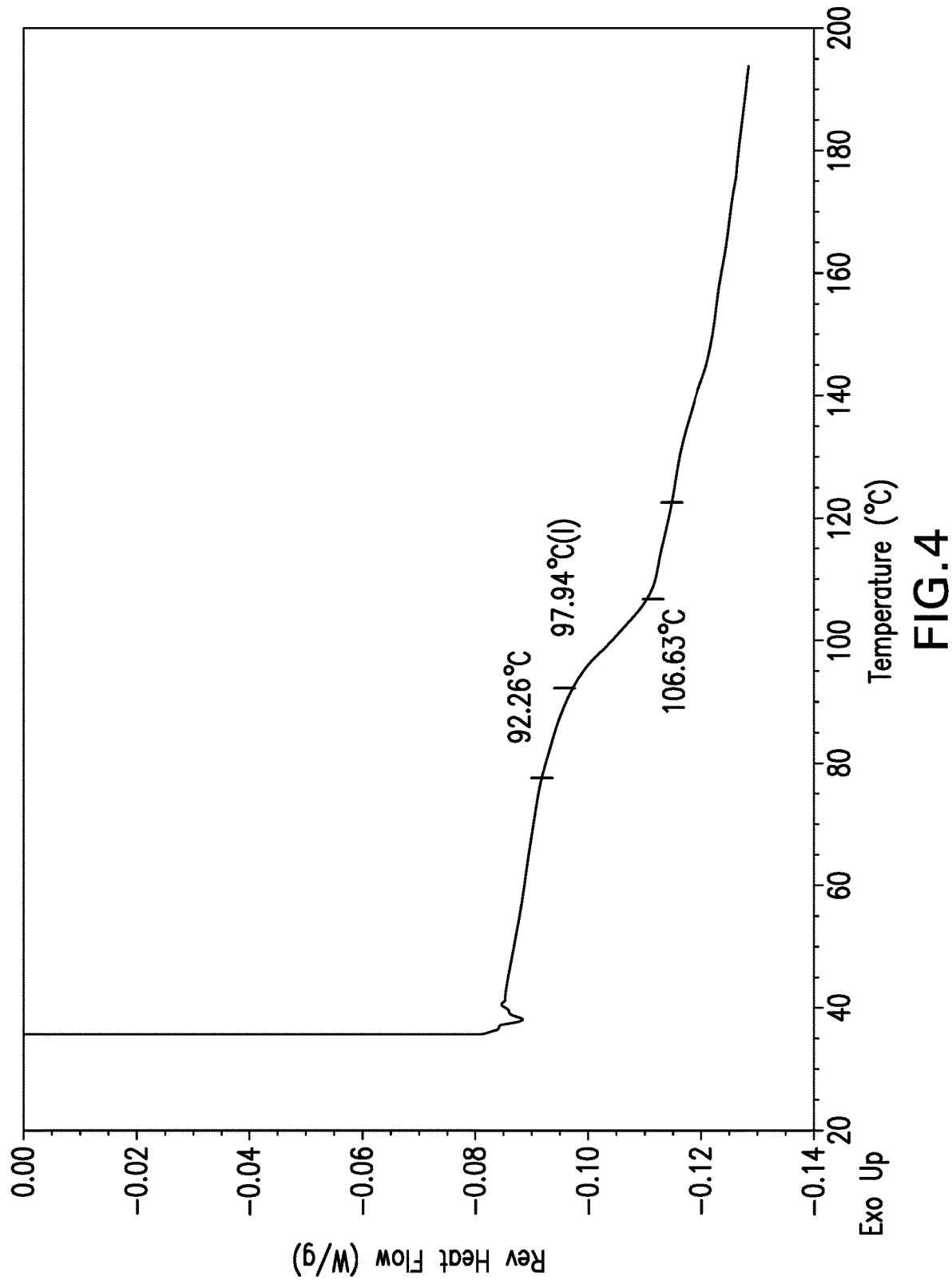
FIG. 4 shows a modulated differential scanning calorimetry (DSC) spectra for the acoustic fusion product of Lopinavir and copovidone Kollido®VA64 with approximate drug loading of 20%, as described in Example 3.

The resulting solids produced from each of the two studies were confirmed to be substantially amorphous using X-ray powder diffraction and DSC ($T_g$ 98° C.). No crystalline peaks were detectable with X-ray powder diffraction and no exothermal peaks were detected using DSC, confirming that the crystalline content in the samples was less than 5%. The X-ray powder diffraction spectra for the acoustic fusion product of Lopinavir and copovidone produced from study 2 is provided in FIG. 3 and the modulated DSC spectra is provided in FIG. 4.

Example 4

Acoustic Mixing of Torcetrapib with Two Different Polymers

Solid model drug Torcetrapib (BCS Class 2) was used for this study, along with solid copovidone polymer Kollidon® VA64 (BASF Corp., Florham Park, N.J.) and waxy solid Vit-E TPGS, which were used as received. 101 mg of Torcetrapib along with 52 mg of Vit-E TPGS and 353 mg of copovidone were each weighed into a 4-mL glass vial at an approximate drug loading of 20%. The mixture was placed in a 24-well heating block element bolted onto the top of a Labram mixer. The heating block was set to 135° C. and the samples were mixed at 80% intensity/~80 G's for 30 minutes before being removed and cooled on the benchtop.

The resulting solid formed a dense, glassy solid, which were confirmed to be substantially amorphous using X-ray powder diffraction, DSC, and microscopy. No crystalline peaks were detectable with X-ray powder diffraction and no exothermal peaks were detected using DSC, confirming that the crystalline content in the sample was less than 5%.

Example 5

In Vivo Absorption of Amorphous Dispersion of Torcetrapib

The in vivo absorption of Torcetrapib after oral administration of the Torcetrapib-copovidone-TPGS dispersion described in Example 4 was investigated in rats at a dose level of 10 mg/kg. Materials and methods used for the rat pharmacokinetic study are provided below. Crystalline drug powders and drug-polymer dispersion formulations were also evaluated as control formulations. The drug powders and drug-polymer dispersions were dosed as suspensions in 0.5% of methylene cellulose. The oral pharmacokinetic parameters are provided in Table 2. The Torcetrapib-polymer dispersion was used as a benchmark formulation for enhancing the drug's solubility and oral absorption. The results showed an increase of approximately 7.8-fold in AUC0-24 compared to the crystalline drug powders.

TABLE 2

Non-Compartmental Pharmacokinetic Parameters After Oral Administration of 10 mg/kg Dose of Torcetrapib Formulations in Rats

| Formulation | $C_{max}$ (μm) | $t_{max}$ (h) | $AUC_{(0-24)}$ (μm*h) | AUC boost* |
|---|---|---|---|---|
| Crystalline torcetrapib powders | 0.084 | 6.0 | 0.707 | 1 |
| Torcetrapib-copovidone -TPGS dispersion | 0.956 | 2.0 | 5.52 | 7.8 |

*Compared to mean $AUC_{(0-24)}$ of crystalline torcetrapib powders
Data are expressed as mean (n = 3).

Oral Administration

Male Wistar-Han rats were used for oral administration studies. All animals were fasted overnight before dosing, provided water ad libitum, and fed 4 hours following drug treatment. The fasted animals were orally given torcetrapib formulations by gavage (n=3) at a torcetrapib dose of 10 mg/kg. The formulations included a suspension of crystalline torcetrapib powder in 0.5% of methyl cellulose (MC), a suspension of torcetrapib-polymer dispersion in 0.5% of acidified MC (5 mM HCl added to prevent dissolution of the polymer in the vehicle). Serial blood samples were collected at 0.25, 0.5, 1, 2, 4, 8, 12, 18, and 24 hour post-dose and placed into EDTA-containing tubes and centrifuged. Plasma was harvested and stored at −70° C. until analysis. All animal procedures were reviewed and approved by the Merck Research Laboratories (MRL)-Institutional Animal Care and Use Committee (IACUC).

Quantification of Plasma Concentration

Torcetrapib plasma concentrations were determined by LC-MS/MS following protein precipitation with acetonitrile. The LC-MS/MS system consisted of a Thermo Scientific LX2 autosampler equipped with two Transcend System pumps (Waltham, Mass., USA) and an Applied Biosystems/MDS Sciex API 5000 mass spectrometer (Foster City, Calif., USA). Chromatographic separation was achieved on an Waters Acquity HSS T3 column (1.8 μm, 2.1×50 mm, Milford, Mass., USA) in conjunction with gradient conditions and mobile phases A (0.1% formic acid in water) and B (0.1% formic acid in acetonitrile). Mass spectrometric detection of the analytes was accomplished using the Turbo Spray interface operated in the positive ion mode. Analyte response was measured by multiple reaction monitoring (MRM) of transitions unique to each compound.

Calibration curves were generated and verified using standard and quality control samples prepared from an initial weighing of high purity compound. For the analysis of the plasma samples, standard samples were prepared by adding 10 μL of standard drug solutions in 1:1 acetonitrile:water (v:v) to 50 μL of control rat plasma with final concentrations ranging from 0.1 to 10,000 ng/mL. The limit of quantification was 1 ng/mL. The calibration curve was prepared by linear regression analysis of the plot of the peak area ratios of torcetrapib to internal standards against the nominal concentrations of torcetrapib. The equation of this curve was used to calculate the drug concentrations in all plasma samples.

Data Analysis

Pharmacokinetic parameters were calculated by established non-compartmental methods. The area under the plasma concentration vs. time curve from time zero to time t(AUC0-t) was determined using the Watson software (version 7.3) with linear trapezoidal interpolation in the ascending slope and logarithmic trapezoidal interpolation in the descending slope.

Example 6

Acoustic Mixing of Model Drug Compound D with HPMCAS-LF Polymer 34 mg of solid model drug Compound D (BCS Class 4, see Example 1) and 67 mg of HPMCAS-LF polymer (hydroxypropylmethylcellulose acetate succinate Grade LF; Shin-Etsu Chemical Co., Ltd., Tokyo, Japan) were weighed into a 4 mL glass vial at an approximate drug loading of 33%. The vial was capped and then placed in the acoustic fusion heating block and clamped down. The sample was then mixed at 60 G's intensity at 150° C. for 30 minutes. Afterwards, the sample was removed and cooled to room temperature.

The resulting solid formed a dense, glassy solid, which were confirmed to be substantially amorphous using X-ray powder diffraction, DSC, and microscopy. No crystalline peaks were detectable with X-ray powder diffraction and no exothermal peaks were detected using DSC, confirming that the crystalline content in the sample was less than 5%.

To further confirm amorphization, improved solubility and physical stability of the amorphous phase, a dissolution experiment of the amorphous solids was run in fasted state simulated intestinal fluid (pH 6.5) to study the dissolution profile (i.e. solubility) over the course of four hours. See Dressman et al., 2000, *Eur. J. Pharm Sci.* 11:73-80. To demonstrate improved solubility in FaSSIF, the solubility of the amorphous dispersion was compared to the FaSSIF solubility of the crystalline drug over the same time course. Drug recrystallization was also monitored through the above mentioned instrumental techniques.

As shown in Table 3, acoustic fusion was able to provide amorphous solid dispersions with complete amorphization and elevated solubility compared to materials produced from simple mixing of the API and polymers, without heating. The solubility of acoustically fused Compound D remained elevated over the time course studied in the fasted simulated intestinal fluid (FaSSIF, pH 6.5).

TABLE 3

Compound D formulation dissolution in FaSSIF at various time points.

| Compound D formulation | Solubility in FaSSIF at various time points (μg/mL) | | | | |
|---|---|---|---|---|---|
| | 0.5 h | 1 h | 2 h | 3 h | 4 h |
| Compound D -API | 61 | 62 | 64 | 66 | 72 |
| 33% Compound D - 67% HPMCAS-L fused at 150° C. | 255 | 214 | 225 | 266 | 271 |
| 33% Compound D - 67% HPMCAS-L mixed with no heating* | 47 | 43 | 46 | 52 | 55 |
| 20% Compound D - 10% TPGS-70% copovidone fused at 160° C. | 215 | 211 | 197 | 191 | 174 |
| 20% Compound D - 80% soluplus fused at 160° C. | 265 | 311 | 447 | 336 | 381 |
| 20% Compound D - 80% soluplus mixed with no heating* | 91 | 124 | 127 | 108 | 83 |

*As a control, the API was mixed with HPMCAS-L (33% drug loading) or soluplus (20% drug loading) on Labram mixer at 60 G for 30 min with no heating.

What is claimed is:

1. A method for producing a stable amorphous dispersion of a drug product comprising:
   a. applying low frequency acoustic energy to a mixture comprising: (i) an active pharmaceutical ingredient (API) and (ii) at least one polymer; and
   b. heating the mixture to a temperature above the glass transition or melting point temperatures of at least one of the polymer or the API to produce a stable amorphous dispersion of the drug product;
wherein the low frequency acoustic energy and the heat are applied to the mixture for a period of time sufficient to form a stable amorphous dispersion of the drug product.

2. The method of claim 1 wherein said low frequency acoustic energy is applied at a frequency of about 10 Hertz to about 100 Hertz.

3. The method of claim 1 wherein said low frequency acoustic energy is applied at a frequency of about 50 Hertz to about 75 Hertz.

4. The method of claim 1, wherein the acoustic energy is applied as a standing wave.

5. The method of claim 1, wherein the acoustic energy imparts a force of from about 10 G to about 100 G.

6. The method of claim 1, wherein the acoustic energy imparts a force of from about 40 G to about 60 G.

7. The method of claim 1, wherein the mixture comprises a secondary polymer.

8. The method of claim 1, further comprising the step of processing the stable amorphous dispersion into a powder using a grinding technique.

9. The method of claim 1, wherein the drug product has a crystalline content of about less than about 5%.

10. The method of claim 1, wherein the polymer is selected from the group consisting of: hydroxypropyl methylcellulose acetate succinate (HPMCAS-LF, HPMCAS-MF, HPMCAS-HF), vitamin E TPGS, polyethylene glycol, methacrylate copolymer, copovidone, polyoxyl 35 hydrogenated castor oil, polyvinyl caprolactam-polyvinyl acetate-polyethylene glycol grafted copolymer, and polyvinylpyrrolidone.

11. The method of claim 1, wherein the API is selected from the group consisting of: megestrol acetate, ciprofloxan, itroconazole, lovastatin, simvastatin, omeprazole, phenytoin, ciprofloxacin, cyclosporine, ritonavir, carbamazepine, carvendilol, clarithromycin, diclofenac, etoposide, budesnonide, progesterone, megestrol acetate, topiramate, naproxen, flurbiprofen, ketoprofen, desipramine, diclofenac, itraconazole, piroxicam, carbamazepine, phenytoin, verapamil, indinavir sulfate, lamivudine, stavudine, nelfinavir mesylate, a combination of lamivudine and zidovudine, saquinavir mesylate, ritonavir, zidovudine, didanosine, nevirapine, ganciclovir, zalcitabine, fluoexetine hydrochloride, sertraline hydrochloride, paroxetine hydrochloride, bupropion hydrochloride, nefazodone hydrochloride, mirtazpine, auroix, mianserin hydrochloride, zanamivir, olanzapine, risperidone, quetiapine fumarate, buspirone hydrochloride, alprazolam, lorazepam, leotan, clorazepate dipotassium, clozapine, sulpiride, amisulpride, methylphenidate hydrochloride, and pemoline.

12. The method of claim 1, wherein the API is anacetrapib, posaconazole, itraconazole, or lopinavir.

13. An amorphous stable drug product prepared in accordance with claim 1.

14. A formulation containing the amorphous drug product of claim 13 in the form of a liquid suspension or solid dosage form.

15. A process for preparing multiple amorphous solid dispersion samples simultaneously, the method comprising:
   (a) loading, into two or more chambers of a multi-chambered apparatus, a mixture comprising: (i) an active pharmaceutical ingredient; and (ii) at least one polymer;
   (b) applying low frequency acoustic energy to said multi-chambered apparatus; and
   (c) heating the apparatus to a temperature above the glass transition or melting point temperature of the mixture in each chamber of the apparatus until said amorphous solid dispersion samples are formed.

16. The process of claim 15, wherein said low frequency acoustic energy is in 10 Hertz to 100 Hertz frequency.

17. The process of claim 15, wherein the acoustic energy is applied as a standing wave.

18. The process of claim 15, wherein the acoustic energy imparts a force of from about 10 G to about 100 G.

19. The process of claim 15, wherein acoustic energy is applied at a frequency of about 60 Hertz.

20. The process of claim 15, wherein each of the stable amorphous solid dispersion samples contains less than about 5% crystalline content.

* * * * *